(12) United States Patent
Suzuki

(10) Patent No.: US 7,884,929 B2
(45) Date of Patent: Feb. 8, 2011

(54) BLADE BREAKAGE AND ABRASION DETECTING DEVICE

(75) Inventor: Tomohiro Suzuki, Mitaka (JP)

(73) Assignee: Tokyo Seimitsu Co., Ltd., Tokyo (JP)

( * ) Notice: Subject to any disclaimer, the term of this patent is extended or adjusted under 35 U.S.C. 154(b) by 163 days.

(21) Appl. No.: 12/410,618

(22) Filed: Mar. 25, 2009

(65) Prior Publication Data
US 2009/0244528 A1 Oct. 1, 2009

(30) Foreign Application Priority Data
Mar. 25, 2008 (JP) ............................. 2008-078484

(51) Int. Cl.
*G01N 21/00* (2006.01)
(52) U.S. Cl. ................................. 356/237.1
(58) Field of Classification Search .... 356/237.1–237.2
See application file for complete search history.

(56) References Cited

U.S. PATENT DOCUMENTS 5,793,493 A * 8/1998 Lane ........................... 356/613

FOREIGN PATENT DOCUMENTS

| JP | 8-164515 A | 6/1996 |
|---|---|---|
| JP | 2000-188267 A | 7/2000 |
| JP | 2006-310396 A | 11/2006 |

* cited by examiner

*Primary Examiner*—Michael P Stafira
(74) *Attorney, Agent, or Firm*—Roberts Mlotkowski Safran & Cole, P.C.; David S. Safran

(57) ABSTRACT

The present invention provides a blade breakage and abrasion detecting device comprising: a detecting unit including a light-emitting unit which is provided close to a side of a blade to emit a round shape light toward the blade, and a light receiving unit which is provided opposed to the light-emitting unit as sandwiching the blade to receive the round shape light from the light-emitting unit with a round shape light receiving area; a moving device which moves the detecting unit toward a rotation center of the blade; and a control unit which detects a breakage of the blade based on a change of an amount of light received by the light receiving unit of the detecting unit, and calculates an abrasion amount of the blade by accumulating a moving amount obtained by controlling the moving device to moves the detecting unit toward the rotation center of the blade.

4 Claims, 8 Drawing Sheets

A-A' CROSS SECTION

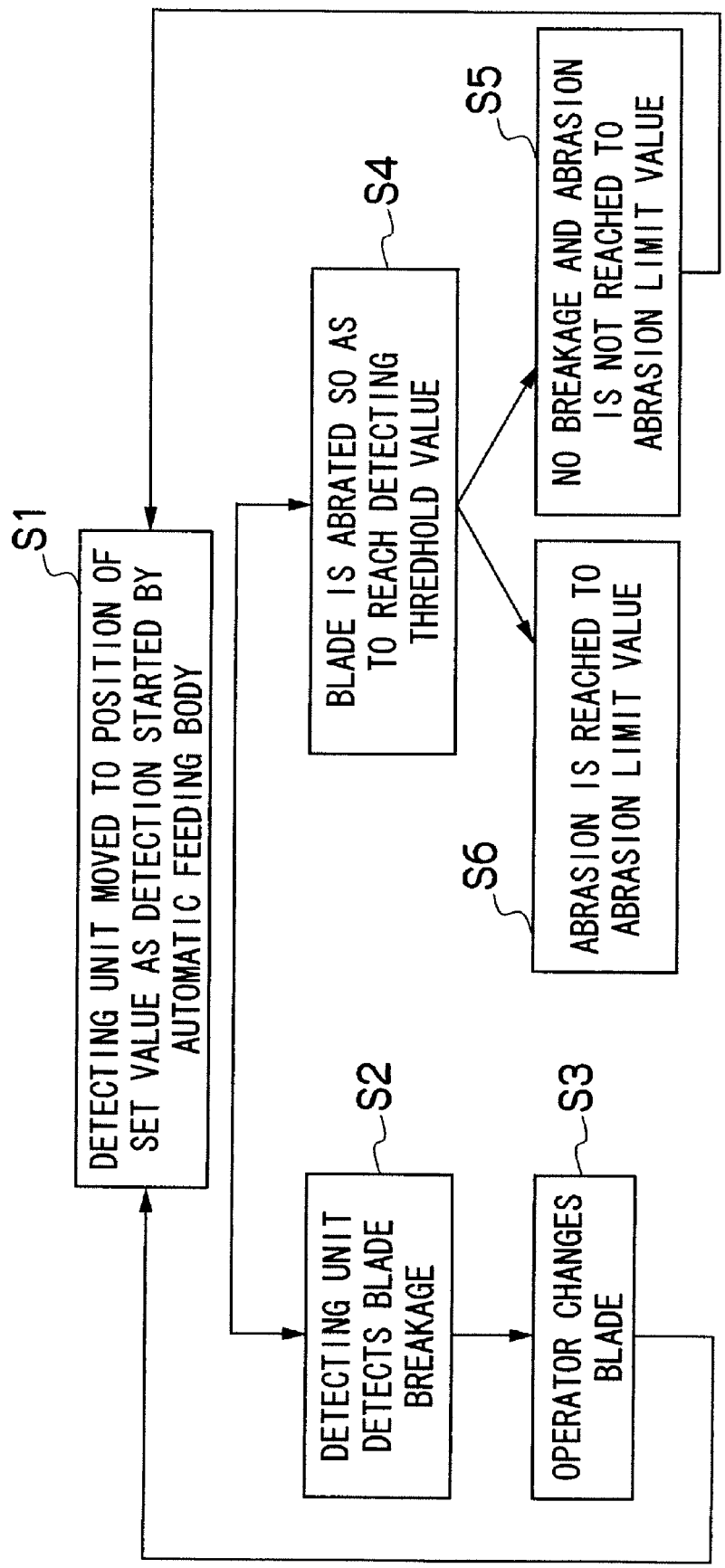

BLADE BREAKAGE AND ABRASION DETECTING DEVICE

BACKGROUND OF THE INVENTION

1. Field of the Invention

The present invention relates to a blade breakage and abrasion detecting device, and more specifically, the invention relates to the blade breakage and abrasion detecting device which automatically detects a breakage and an abrasion of a blade of a dicing apparatus.

2. Description of the Related Art

A dicing apparatus which divides a work having a semiconductor device and an electronic element formed thereon into a chip comprises a blade which is rotated at high speed by a spindle, a table which holds the work with suction, X, Y, Z, and θ axes which are the axes of motion changing a relative position of the table and the blade. The dicing apparatus grooves and cuts the work which is held on the table with suction and is relatively moved by each axis with the blade which rotates at high speed.

The blade is gradually abraded because of a work load at the blade when the dicing apparatus processes the work, and the blade is broken at the processing when there is a large work load at the blade. A depth of a groove processed with the blade is changed when the processing is continued with the abraded blade, so a grooving process with a predetermined depth and an assured cutting process can not be performed. Also, it becomes a cause of damaging the workpiece that the processing is continued with the broken blade.

To solve such a problem, a device which detects an amount of an abrasion of a blade by detecting an amount of moving down of the blade when the blade is moved down between a light-emitting unit and a light receiving unit which are provided opposed having a predetermined space in the middle is disclosed in Japanese Patent Application Laid-Open No. 8-164515. In addition, as disclosed in Japanese Patent Application Laid-Open No. 2000-188267, the light-emitting unit and the light receiving unit are provided opposed as sandwiching the rotating blade and the breakage of the blade is detected by detecting the change of the amount of the light received at the light receiving unit.

However, it is necessary to suspend the processing of the work, move the blade to the abrasion amount detecting device provided the position separated from the table, and move up and down the blade, in order to detect the abrasion amount of the blade with the abrasion amount detecting device of Japanese Patent Application Laid-Open No. 8-164515, thereby a processing efficiency is decreased. The light transmitted to a light-emitting area of the light-emitting unit of a blade breakage detector is small and round at the abrasion amount detecting device of Japanese Patent Application Laid-Open No. 2000-188267, so the peak of the detection sensitivity is narrow with the condition and it is necessary to adjust the height depending on the outstanding length of the blade.

Therefore, Japanese Patent Application Laid-Open No. 2006-310396 discloses a blade breakage and abrasion detecting device including the light-emitting unit and the light receiving unit provided near by the side of the blade of the dicing apparatus. The light-emitting area of the light-emitting unit and the light receiving area of the light receiving unit have the length equal to or longer than the length of the blade which is outstanding from a flange, and are rectangular shape areas having a longer side toward the rotation center of the blade.

It is possible to detect the blade breakage and abrasion by detecting the change of the amount of light received with the light receiving area of the light receiving unit according to the blade breakage and abrasion detecting device. At this time, the light-emitting area of the light-emitting unit and the light receiving area of the light receiving unit have the length equal to or longer than the outstanding length of the blade toward the rotation center of the blade, so there is no need to adjust the positions of the light-emitting unit and the light receiving unit according to the outstanding length of the blade. Moreover, there is unnecessary to move the blade to the abrasion amount detecting device because it is possible to calculate the abrasion amount based on the increased amount of the received light. Additionally, it is possible to detect the blade breakage according to the rapid change of the amount of the received light during processing and the abrasion amount of the blade according to the increased amount of the received light even during processing.

SUMMARY OF THE INVENTION

A commonly used blade breakage detecting device includes a light-emitting unit which emits a round shape light to a blade and a light receiving unit which receives the light from the light-emitting unit with a light receiving area with a round shape which is provided opposed to the light-emitting unit with sandwiching the blade. The diameter of the round shaped light receiving area of the light receiving unit is approximately 1 mm. The light receiving unit has a sensitivity which is able to detect a fine partial breakage as small as a square about 0.5 mm on a side.

However, a flange cover which is attached the blade breakage detecting device on is in a state that the blade breakage detecting device is ordinary watered with a cutting water and a cooling water during cutting. Therefore, there is a time where the fine partial breakage cannot be detected because of the influence of the water.

There is a case where the fine partial breakage cannot be detected even with the round shape light receiving area, so there are more cases that the blade breakage cannot be detected with the light receiving unit having the rectangular light receiving area like Japanese Patent Application Laid-Open No. 2006-310396 because the detection area becomes larger and the detection sensitivity has blurring (the detection sensitivity becomes lower).

The present invention has been made in view of the above circumstances and has an object to provide a blade breakage and abrasion detecting device which makes it possible to detect the blade breakage and the abrasion amount at the same time with the detection sensitivity as it stands with eliminating adjusting the position of the detecting unit which has been performed by an operator conventionally.

To achieve the object above, the present invention provides a blade breakage and abrasion detecting device comprising: a detecting unit including a light-emitting unit which is provided close to a side of a blade to emit a round shape light toward the blade, and a light receiving unit which is provided opposed to the light-emitting unit as sandwiching the blade to receive the round shape light from the light-emitting unit with a round shape light receiving area; a moving device moves the detecting unit toward a rotation center of the blade; and a control unit detecting a breakage of the blade based on a change of an amount of light received by the light receiving unit of the detecting unit, and calculating an abrasion amount of the blade by accumulating a moving amount obtained by controlling the moving device to move the detecting unit toward the rotation center of the blade.

According to the present invention, the control unit detects the blade breakage based on the amount of light received by the round shape light receiving area of the light receiving unit having a sensitivity of the light receiving as of this date. Then, the control unit calculates the abrasion amount of the blade by accumulating the moving amount obtained by controlling the moving device to move the detecting unit toward the rotation center of the blade automatically.

Thus, according to the present invention, it is possible to detect the blade breakage and the abrasion amount at the same time with keeping the detection sensitivity as it stands with eliminating adjusting the position of the detecting unit which has been performed by an operator conventionally.

In addition, according to the present invention, the blade breakage and abrasion detecting device is characterized in that the control unit records a first amount of light received by the light receiving unit as a threshold value of the amount of received light, and a second amount of received light which is larger than the first amount of received light. It is preferable that the control unit moves the detecting unit by controlling the moving device toward the rotation center of the blade when the amount of received light by the light receiving unit reaches the second amount of received light, and stops moving the detecting unit by controlling the moving device when the amount of light received by the light receiving unit reaches the first amount of received light during the work processed by the blade.

According to the present invention, when the amount of light received by the light receiving unit reaches to the second amount of received light during the work processing by the blade, the control unit moves the detecting unit by controlling the moving device toward the rotation center of the blade, and stops moving the detecting unit by controlling the moving device when the amount of received light reaches the first amount of received light. The abrasion amount of the blade can be obtained by accumulating the moving amount. Additionally, the set value of the amount of light received by the light receiving unit with mounting or exchanging the new blade for the old one may be the first amount of received light, but it can be other values smaller than the second amount of received light.

Moreover, it is preferable that the control unit stops moving the detecting unit by controlling the moving device when the accumulated moving amount of the detecting unit reaches an abrasion limit value which is set beforehand.

According to the present invention, when the accumulated moving amount of the detecting unit reaches an abrasion limit value which is set beforehand, the control unit stops moving the detecting unit by controlling the moving device so that it is prevented that the detecting unit hits a flange of the blade.

The blade breakage and abrasion detecting device of the present invention makes it possible to detect the blade breakage and the abrasion amount at the same time with the detection sensitivity as it stands with eliminating adjusting the position of the detecting unit which has been performed by an operator conventionally.

BRIEF DESCRIPTION OF THE DRAWINGS

FIG. 8 is a flow chart showing a performance of the blade breakage and abrasion detecting device.

DETAILED DESCRIPTION OF THE PREFERRED EMBODIMENT

Referring to the accompanying drawings, a detailed description will be given below of preferred embodiments of a blade breakage and abrasion detecting device according to the present invention.

Figure 1:
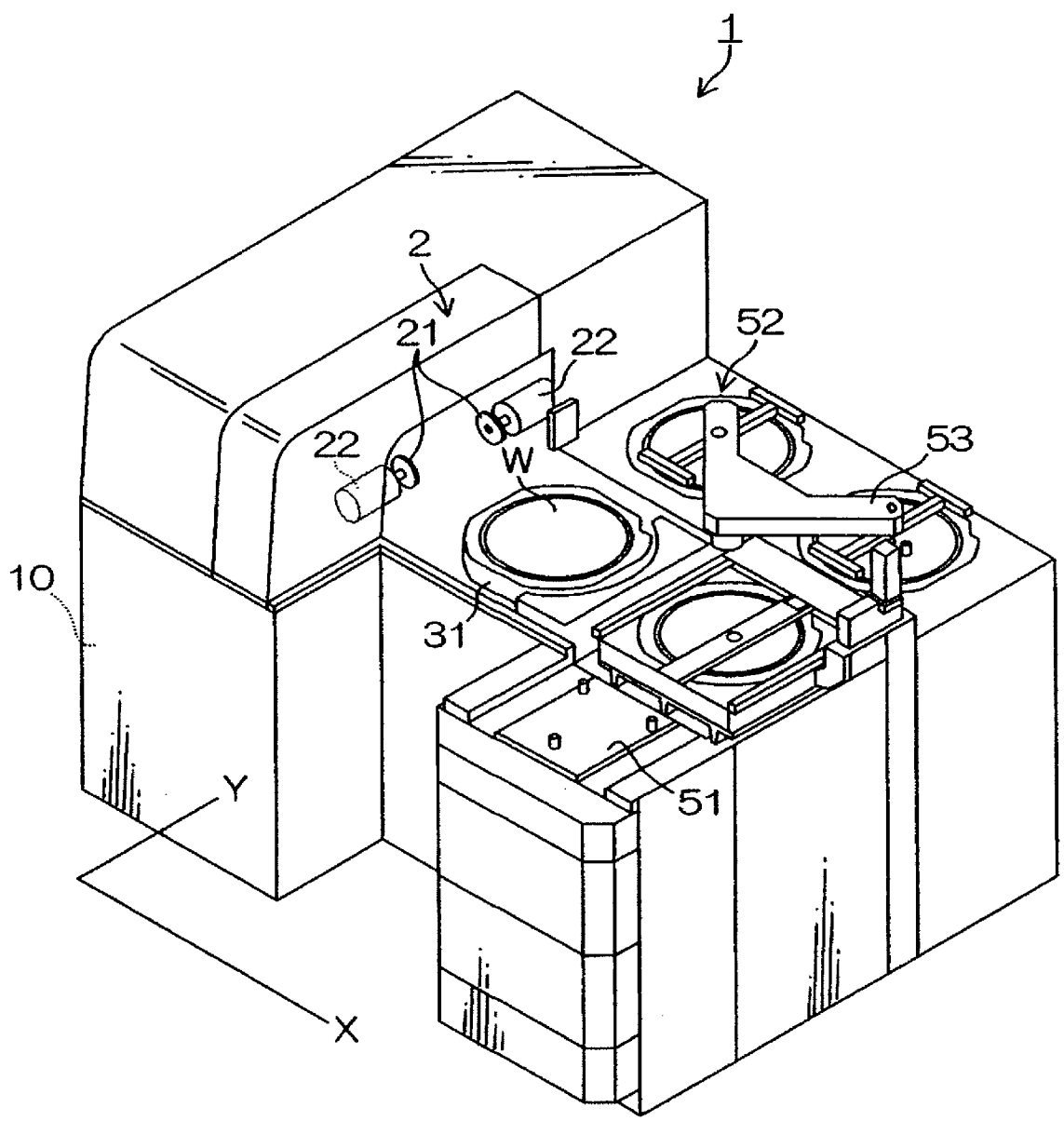
FIG. 1 is a perspective view showing an exterior of a dicing apparatus which includes a blade breakage and abrasion detecting device of the present embodiment.

FIG. 1 is a perspective view showing an exterior of a dicing apparatus 1 which includes the blade breakage and abrasion detecting device of the present embodiment. The dicing apparatus 1 comprises a spindle 22, 22 having an incorporated high frequency motor, which is provided opposed to each other and having a blade 21 and a wheel cover (not shown) mounted at its end, a processing unit 2 having a work table 31 which holds a work W with suction, a cleaning unit 52 cleaning the processed work W by spinning, a load port 51 loading a cassette storing a number of the works W, a moving device 53 moving the work W, and a control unit 10 controlling integrally a performance of each unit.

Figure 2:
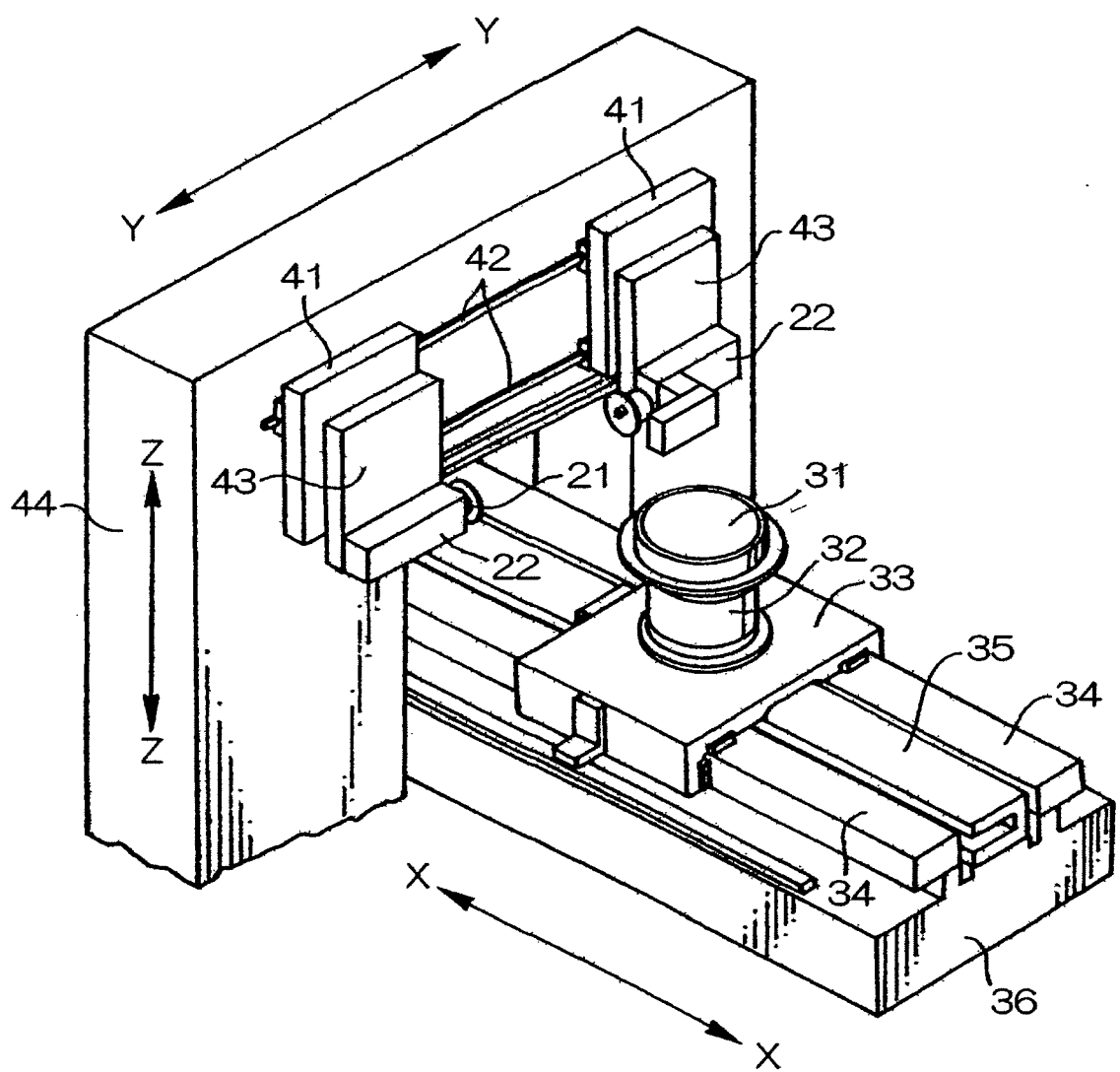
FIG. 2 is a perspective view showing a configuration of a processing unit of the dicing apparatus shown in FIG. 1.

As shown in FIG. 2, the processing unit 2 has a X table 33 which is guided by a X guide 34, 34 provided on a X base 36 and driven in the X direction shown with X-X in FIG. 2 by a linear motor 35, and a work table 31 is provided on the X table 33 through a rotating table 32 which rotates in the θ direction.

On the other hand, a Y table 41, 41 is provided on a side of a Y base 44 which is provided as being stride over the linear motor 35. The Y table 41, 41 is guided by a Y guide 42, 42, and driven by a stepping motor and a ball screw which are not shown in a Y direction shown as Y-Y in the drawing. A Z table 43 which is driven in a Z direction by an unshown driving device is provided at each Y table 41. Also the spindle 22 with an incorporated high frequency motor having the blade 21 at the end is mounted on the Z table 43. In this configuration of the processing unit 2, the blade 21 is index-fed in the Y direction and fed to cut into in the Z direction, and the work table 31 is fed to cut in the X direction.

The control unit 10 which controls integrally the performance of each unit of the dicing apparatus 1 includes a CPU, a memory, an in/output circuit unit, and various control circuit units, and is incorporated in a mount of the dicing apparatus.

Figure 3:
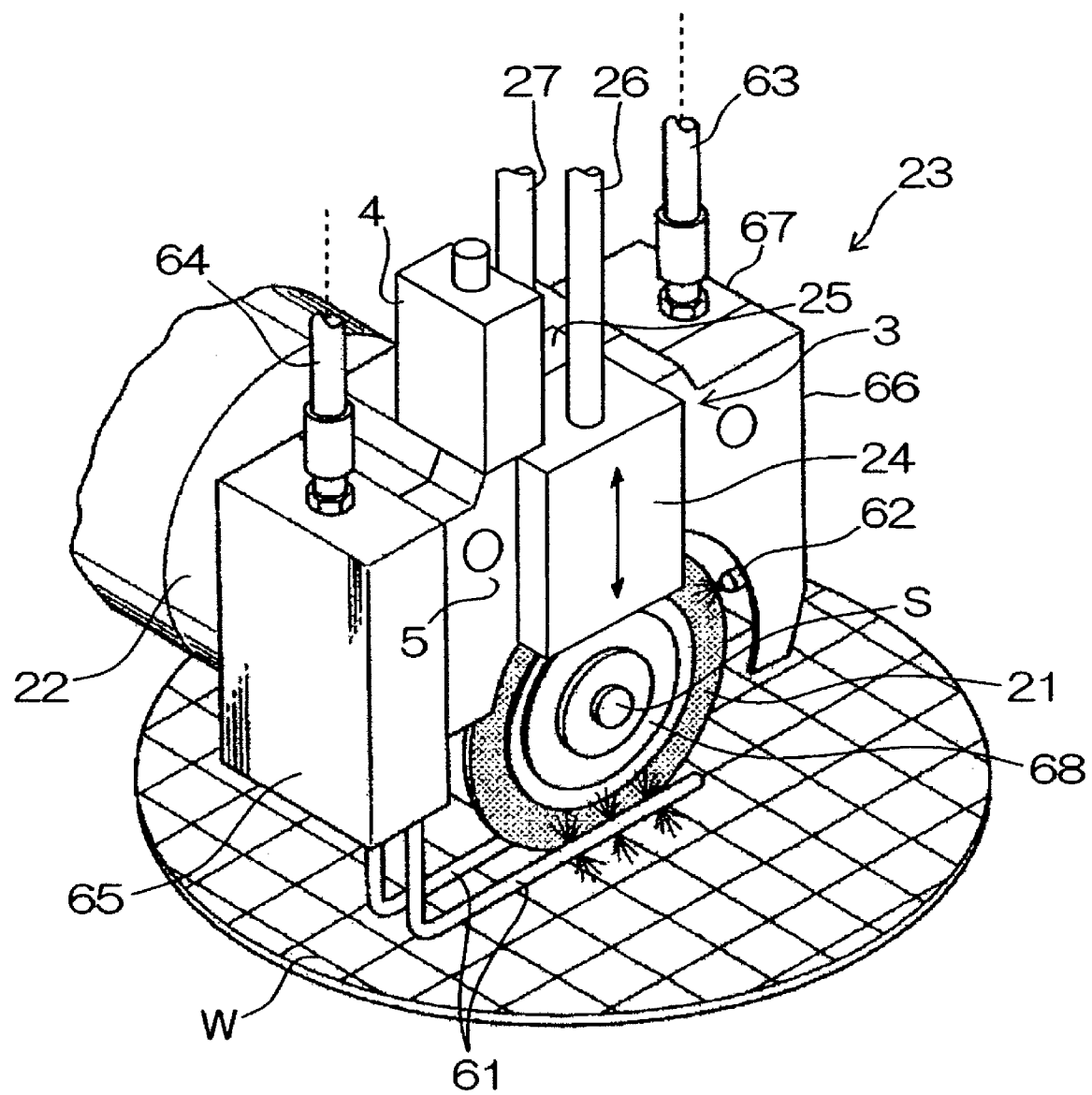
FIG. 3 is a perspective view of an end of a spindle of the dicing apparatus shown in FIG. 1.
Figure 4A:
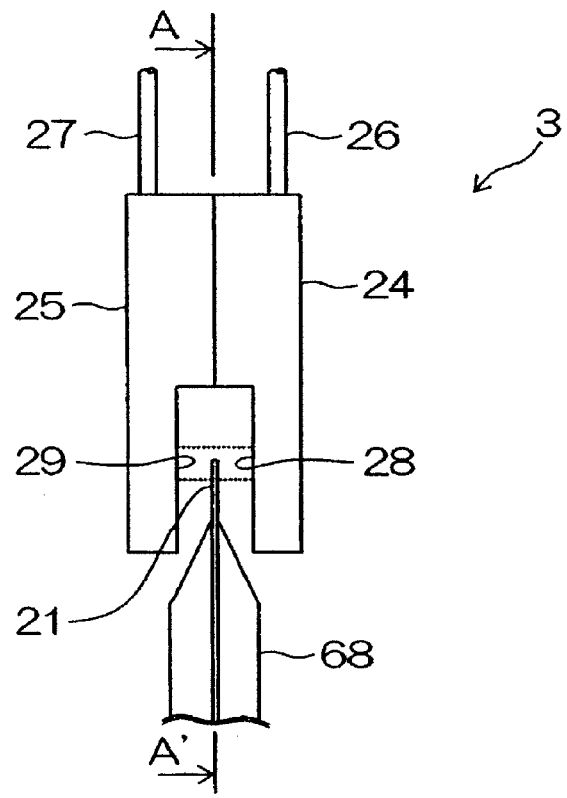
FIGS. 4A and 4B are a side view and a cross section view showing typically a configuration of a detecting unit of the blade breakage and abrasion detecting device.
Figure 4B:
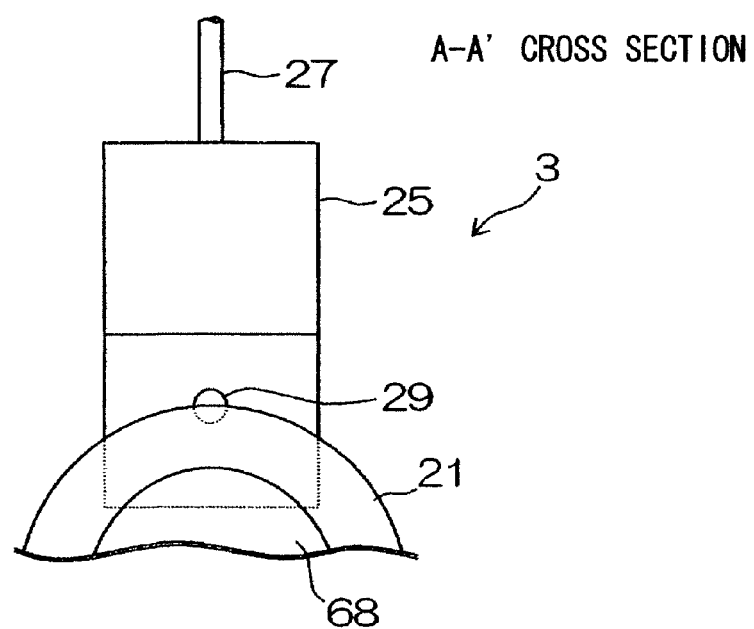

Next, the configuration of the blade breakage and abrasion detecting device of the present embodiment is described referring to FIGS. 3 to 4B.

FIG. 3 is a perspective view showing the configuration of the end of the spindle 22 which includes a detecting unit 3 of the blade breakage and abrasion detecting device and a feeding body 4, and FIGS. 4A and 4B are a side view and a cross section view showing typically the configuration of the detecting unit 3.

A wheel cover 23 is provided at the end of the spindle 22 to cover the blade as shown in FIG. 3. The wheel cover 23 includes a cover front section 66, a cover rear section 67, a nozzle block 65, and so on. A plurality of hoses 63, 64 are connected to the cover rear section 67 and the nozzle block 65, a cutting water is supplied through the hoses 63, 64, and the supplied cutting water is sprayed from a plurality of nozzles 61, 62 to the blade 21 which is rotating.

As described above, the blade breakage and abrasion detecting device includes the detecting unit 3, the feeding body 4 and the control unit 10 shown in FIG. 1.

As shown in FIG. 4A, the detecting unit 3 includes a light-emitting unit 24 and a light receiving unit 25, and the light-emitting unit 24 and the light receiving unit 25 are attached to the wheel cover 23 in FIG. 3 with facing each other as sandwiching the blade 21. The light-emitting unit 24 and the light receiving unit 25 are integrated as the detecting unit 3 and supported to be raised and lowered by a guide block of the wheel cover 23. In addition, the feeding body 4 which is a moving device of the detecting unit 3 is mounted to the wheel cover 23, and the detecting unit 3 is moved in the vertical direction of the FIGS. 3 to 4B by the drive force of the feeding body 4. In this manner, a round shape light-emitting area 28 of the light-emitting unit 24 and a light receiving area 29 having a round shape about 1 mm in diameter as shown in FIG. 4B are integrally moved straight toward the rotation center S of the blade. A feed screw, a ball screw and so on can be employed as the feeding body 4.

An optical cable 26 which is connected to a light source (not shown) with one end is connected the light-emitting unit 24 with another end. The light transmitted from the light source through the optical cable 26 is emitted toward the blade 21 through the round shape light-emitting area 28 formed on the surface of the light-emitting unit 24 facing to the blade 21.

On the other hand, an optical cable 27 connected to an amplifier device (not shown) which converts a light signal into an electric signal is connected to the light receiving unit 25 with another end. The light emitted from the light-emitting area 28 of the light-emitting unit 24 is received at the light receiving area 29 having a round shape formed on the light receiving unit 25, and transmitted to the amplifier device through the optical cable 27. The transmitted light is converted into the electric signal by the amplifier device and sent to the control unit 10. The size of the electric signal changes according to the amount of the light received at the light receiving area 29.

Next, the function of the blade breakage and abrasion detecting device is explained.

The dicing apparatus 1 having the blade breakage and abrasion detecting device cuts a work having a semiconductor device and an electronic element formed thereon into a grid state or performs a grooving process with the blade 21 mounted at the end of the spindle 22. The wheel cover 23 is attached to the spindle 22 as covering the blade 21, and the cutting water is splayed toward the blade 21 with the nozzle 61, 62 which is provided at the wheel cover while the work W is being processed.

The detecting unit 3 of the blade breakage and abrasion detecting device is attached to the wheel cover 23 so that the light-emitting unit 24 and the light receiving unit 25 sandwich the blade 21 as shown in FIG. 4A. The round shape light emitted from the light-emitting area 28 of the light-emitting unit 24 is blocked off partially by the blade 21 and received by the round shape light receiving area 29 of the light receiving unit 25. The received light is converted into the electric signal by the amplifier device (not shown) according to the amount of the received light.

With the dicing apparatus 1 before starting the work process, it is performed as a calibration process that the rotating blade 21 is slightly touched to the work table 31, the distance from the origin position of the blade to the work table 31 is recorded, and at the same time, the amount of light received by the light amount area 29 is recorded. The feeding amount to cut into in the Z direction with the blade 21 is adjusted according to the data such as the value obtained by the calibration process, the diameter of the blade 21 which is input beforehand, a work thickness, and a tape thickness.

The process of the work W is started after finishing the calibration process. The control unit 10 monitors the change of the amount of received light at the light receiving area 29 as the change of the electric signal transmitted from the amplifier device continually. The control unit 10 determines that the blade 21 is broken, when the electric signal is rapidly changed, or when the signal which shows that the amount of received light is larger than the other part is periodically generated. Then, the control unit 10 stops the rotation of the blade, and raises the spindle 22. In this way, the blade breakage and abrasion detecting device of the present embodiment is able to detect the breakage of the blade 21.

By the way, the control unit 10 controls the feeding body 4 according to the change of the amount of light received by the light receiving unit 25 to feed the detecting unit 3 toward the rotation center of the blade automatically. Then, the control unit 10 calculates the abrasion amount of the blade 21 by accumulating the moving amount of the detecting unit 3.

Specifically, the control unit 10 records a first amount of received light as a threshold value of the amount of light received by the light receiving unit 25 (for example, 10% of the light receiving area), and a second amount of received light (for example, 60% of the light receiving area) which is larger than the first amount of received light.

Figure 6:
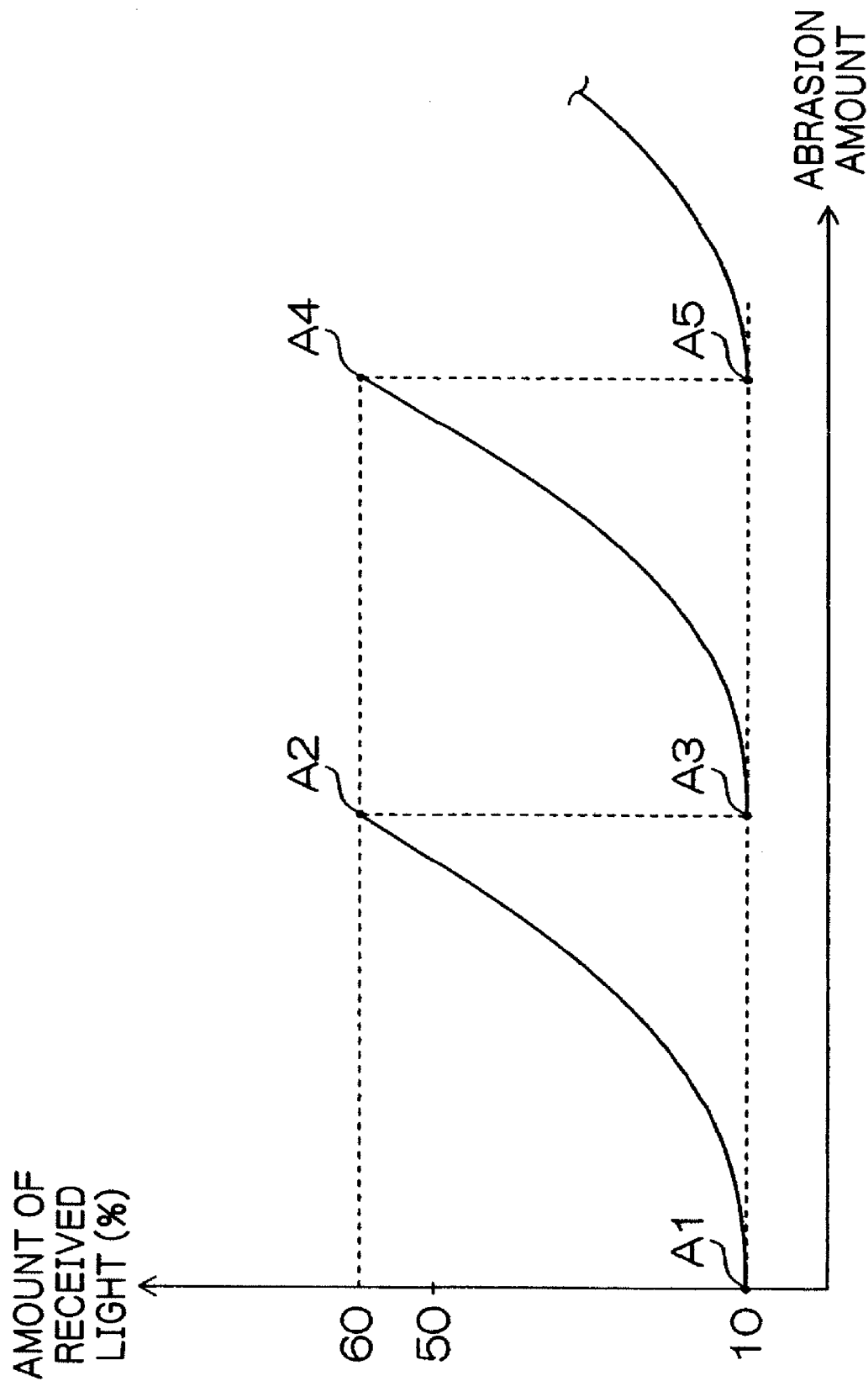
FIG. 6 is a graph showing a relation between an abrasion amount of a blade and an amount of a received light.

As shown in the graph of FIG. 6, when the amount of light received by the light receiving area 29 of the light receiving unit 25 is set 10% at a process start point A1 (as shown as A1 in FIG. 7), the detector (the detecting unit) 3 is moved to the position of the set value as the detection started by the automatic feeding body 4. After that, the processing of the work W by the blade 21 is started, and then the blade 21 abrades away gradually because of the work load on the work W so that makes the diameter smaller.

The blade 21 is changed by an operator (referring to FIG. 8 (S3)) when the detecting unit 3 detects the breakage of the blade 21 as described above during the processing with the blade 21 (referring to FIG. 8 (S2)).

Figure 7:
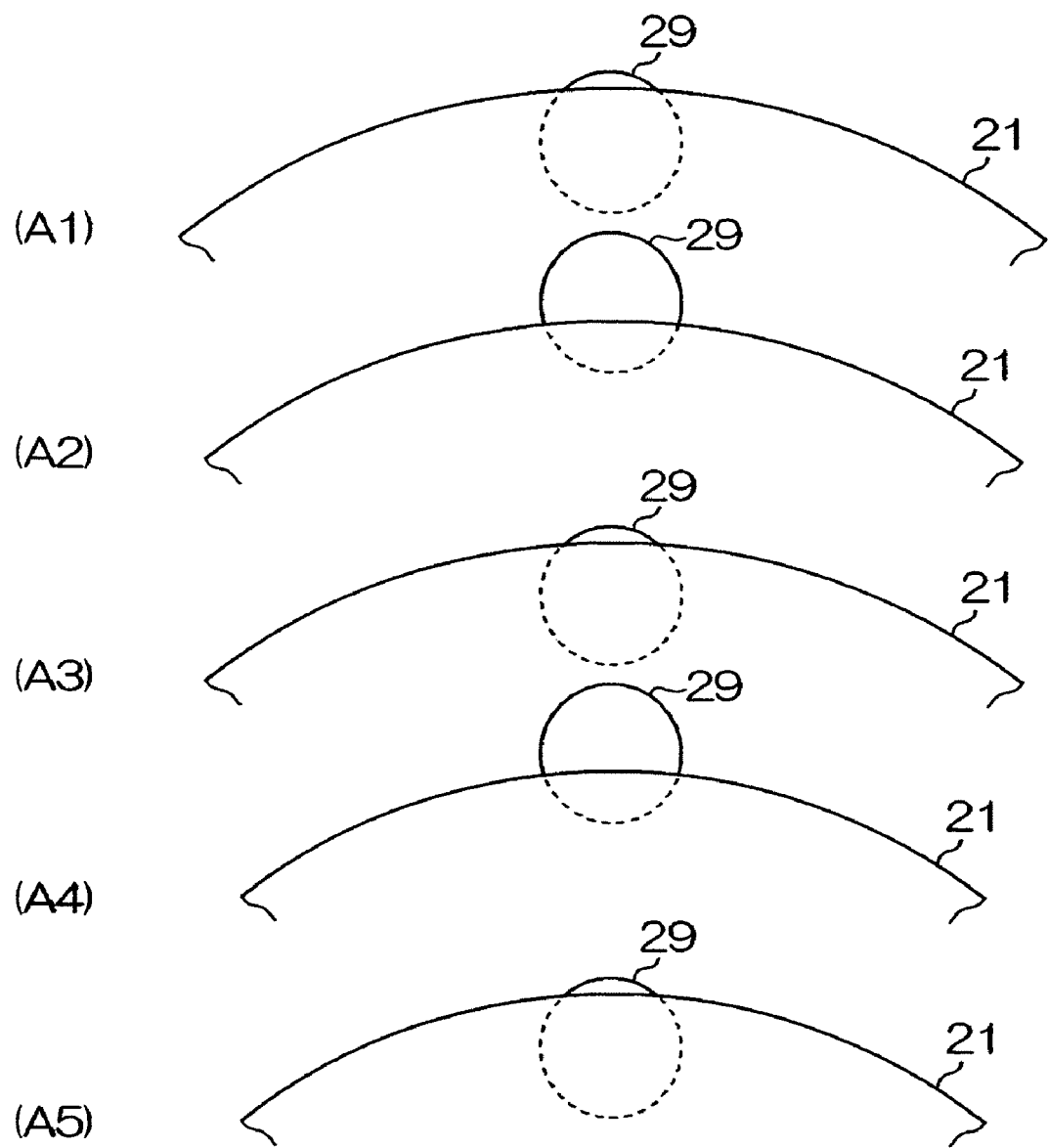
FIG. 7 is an explanatory diagram showing a positional relation between the abrasion amount of the blade and a light receiving area.

On the other hand, the control unit 10 controls the feeding body 4 to feed the detecting unit 3 toward the rotation center of the blade automatically, when the process is continued without having the breakage of the blade 21 and the amount of light received by the light receiving unit 25 with the light receiving area 29 becomes 60% (referring to FIG. 6 (A2), FIG. 7 (A2), and FIG. 8 (S4)). Then, the control unit 10 controls the feeding body 4 to stop moving the detecting unit 3 when the amount of light received by the light receiving area 29 becomes 10% (referring to FIG. 6 (A3), FIG. 7 (A3), and FIG. 8 (S5)). Specifically, the control unit 10 controls the feeding body 4 to move the detecting unit 3 to the position of the set value as the detection started (referring to FIG. 8 (S1)) because the blade 21 is not broken or the abrasion amount is not reached to an abrasion limit value which is set beforehand (referring to FIG. 8 (S5)). The process of the work W is continuing during the period above.

The control unit 10 controls the feeding body 4 to feed the detecting unit 3 toward the rotation center of the blade automatically when the amount of light received by the light receiving area 29 becomes 60% in accordance with the abrasion of the blade 21 (referring to FIG. 6 (A4) and FIG. 7 (A4)). As the amount of light received by the light receiving area 29 becomes 10% (referring to FIG. 6 (A5) and FIG. 7 (A5)), the control unit 10 controls the feeding body 4 to stop moving the detecting unit 3. The control unit 10 calculates the abrasion amount of the blade 21 by accumulating the moving amount of the detecting unit 3 at moving repeatedly, and displays the abrasion amount on a display device (not shown in the drawings).

Figure 5:
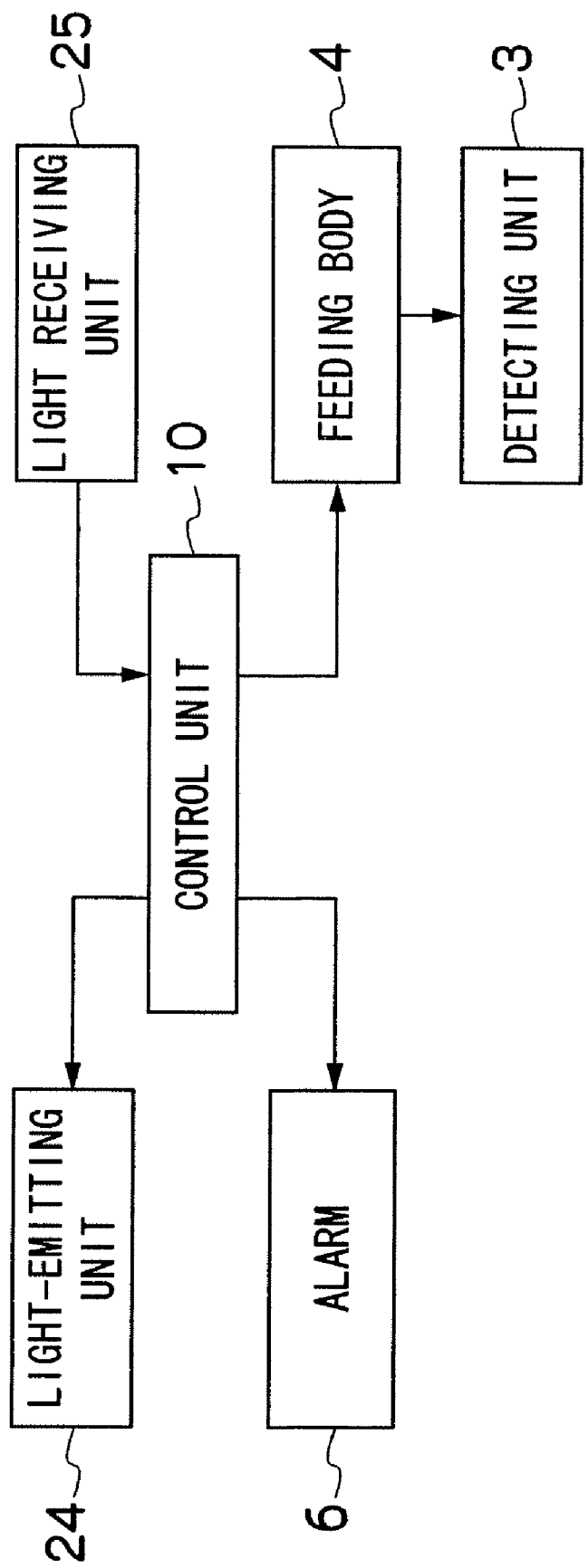
FIG. 5 is a block diagram showing a composition of the blade breakage and abrasion detecting device.

The control unit 10 controls the feeding body 4 to stop moving the detecting unit 3 and controls an alarm 6 (shown in FIG. 5) to issue an alert to change the blade when the accumulated moving amount of the detecting unit 3 reaches the abrasion limit value which is set beforehand (referring to FIG. 8 (S6)). Then, the operator changes the blade 21 (FIG. 8 (S3)).

Therefore, a failure that the detecting unit 3 hits a flange 68 of the blade 21 which resulted from an overrun of the detecting unit 3 can be prevented by stopping the detecting unit 3 mandatorily. Additionally, the set value of the amount of light received by the light receiving unit 25 with mounting or exchanging the new blade 21 for the old one may be the first amount of received light, but it can be other values smaller than the second amount of received light.

As explained above, the blade breakage and abrasion detecting device of the present embodiment makes it possible to detect the blade breakage and the abrasion amount at the same time with the detection sensitivity as it stands with eliminating adjusting the position of the detecting unit 3 which has been performed by the operator conventionally.

The light-emitting area 28 and the light receiving area 29 has round shape in the present embodiment but they can be square having an area nearly equal to the light-emitting area 28 and the light receiving area 29.

What is claimed is:

1. A blade breakage and abrasion detecting device comprising:
    a detecting unit including a light-emitting unit which is provided close to a side of a blade to emit a round shape light toward the blade, and a light receiving unit which is provided opposed to the light-emitting unit as sandwiching the blade to receive the round shape light from the light-emitting unit with a round shape light receiving area;
    a moving device which moves the detecting unit toward a rotation center of the blade; and
    a control unit which detects a breakage of the blade based on a change of an amount of light received by the light receiving unit of the detecting unit, and calculates an abrasion amount of the blade by accumulating a moving amount obtained by controlling the moving device to move the detecting unit toward the rotation center of the blade.

2. The blade breakage and abrasion detecting device according to claim 1, wherein
    the control unit records a first amount of light received by the light receiving unit as a threshold value of an amount of received light, and a second amount of received amount which is larger than the first amount of received light, moves the detecting unit by controlling the moving device toward the rotation center of the blade when the amount of light received by the light receiving unit reaches the second amount of received light, and stops moving the detecting unit by controlling the moving device when the amount of light received by the light receiving unit reaches the first amount of received light during the work processed by the blade.

3. The blade breakage and abrasion detecting device according to claim 1, wherein
    the control unit stops moving the detecting unit by controlling the moving device when the accumulated moving amount of the detecting unit reaches an abrasion limit value which is set beforehand.

4. The blade breakage and abrasion detecting device according to claim 2, wherein
    the control unit stops moving the detecting unit by controlling the moving device when the accumulated moving amount of the detecting unit reaches an abrasion limit value which is set beforehand.

* * * * *